(12) United States Patent
Lovoi

(10) Patent No.: US 11,154,363 B1
(45) Date of Patent: Oct. 26, 2021

(54) TERMINAL GUIDANCE FOR IMPROVING THE ACCURACY OF THE POSITION AND ORIENTATION OF AN OBJECT

(71) Applicant: Paul A. Lovoi, Saratoga, CA (US)

(72) Inventor: Paul A. Lovoi, Saratoga, CA (US)

( * ) Notice: Subject to any disclaimer, the term of this patent is extended or adjusted under 35 U.S.C. 154(b) by 310 days.

(21) Appl. No.: 15/604,551

(22) Filed: May 24, 2017

Related U.S. Application Data

(60) Provisional application No. 62/340,925, filed on May 24, 2016.

(51) Int. Cl.
*A61B 34/20* (2016.01)
*A61B 34/00* (2016.01)

(52) U.S. Cl.
CPC .............. *A61B 34/20* (2016.02); *A61B 34/25* (2016.02); *A61B 2034/2048* (2016.02); *A61B 2034/2072* (2016.02)

(58) Field of Classification Search
None
See application file for complete search history.

(56) References Cited

U.S. PATENT DOCUMENTS

| 6,351,659 | B1 | 2/2002 | Vilsmeier | |
|---|---|---|---|---|
| 9,947,091 | B2 * | 4/2018 | Govari | A61B 6/032 |
| 10,154,882 | B2 * | 12/2018 | Garbey | A61B 17/3421 |
| 2012/0078236 | A1 * | 3/2012 | Schoepp | A61B 34/20 606/1 |
| 2013/0218137 | A1 * | 8/2013 | Abovitz | A61B 90/98 606/1 |
| 2014/0243658 | A1 * | 8/2014 | Breisacher | A61B 5/061 600/424 |
| 2014/0275760 | A1 * | 9/2014 | Lee | A61B 34/30 600/102 |
| 2015/0018622 | A1 * | 1/2015 | Tesar | A61B 1/05 600/202 |

OTHER PUBLICATIONS

Khoshnevisan, A. et al., Neuronavigation: Principles, Clinical Applications and Potential Pitfalls, Iranian Journal of Psychiatry, 2012; 7:97-103, Tehran University of Medical Sciences (www.tums.ac.ir).

* cited by examiner

*Primary Examiner* — Angela M Hoffa
*Assistant Examiner* — Younhee Choi
(74) *Attorney, Agent, or Firm* — Thomas M. Freiburger

(57) ABSTRACT

A method of locating a tool or device uses vision driven navigation augmented by inertial guidance. The vision navigation is in reference to fiducial markers in a room viewed by cameras mounted on the tool or device. The cameras calculate the location of the tool or device based on the fiducial markers. The combination of a camera fiducial location and inertial guidance assures knowing the tool's location and orientation regardless of interruption of line-of-sight. Using combined guidance provides a more robust and precise tool or device location and pointing. MEMS sensors and smart phone cameras can be used to make compact tools or devices.

2 Claims, 8 Drawing Sheets

TERMINAL GUIDANCE FOR IMPROVING THE ACCURACY OF THE POSITION AND ORIENTATION OF AN OBJECT

This application claims benefit of provisional application Ser. No. 62/340,925, filed May 24, 2016.

BACKGROUND OF THE INVENTION

The invention concerns surgical techniques and apparatus, and in particular a means of determining placement and path of a surgical tool.

Referencing systems in the sense of this application are known for example from, Khoshnevisan A., Sistany Allahabadi N. Neuronavigation: Principles, Clinical Applications and Potential Pitfalls, Iranian Journal of Psychiatry, 2012; 7(2):97-103, the content of the disclosure of which is explicitly incorporated by way of reference in the present application. Such systems are known as navigation systems, providing the surgeon carrying out the treatment, using diagnostic data obtained for example from CAT scans and represented visually by an image output on a computer display, navigation information useful for carrying out the surgery. For detecting three-dimensional spatial co-ordinates, a plurality of markers with known dimensions are used, such as are, for example, described in U.S. Pat. No. 6,351,659. A radiation source, in particular an infrared radiation source, illuminates the area in which three-dimensional spatial co-ordinates are to be determined, and the radiation reflected by the markers is detected with the aid of at least two cameras, each from a different angle of view. Alternatively, the objects to be referenced can also actively emit radiation, in particular infrared radiation, to which end radiation sources, for example LEDs, are attached to the objects, the radiation from which is detected as described above. The camera signals are evaluated with the aid of a subordinated computational unit and by means of known algorithms.

It is necessary for referencing devices used in the surgery that there are always at least two cameras monitoring the area in which three-dimensional spatial co-ordinates are to be determined, from different angles of view, without the relevant field of view of the cameras being obscured.

In many situations, this can be difficult. In an operating theater, the suitable position for the cameras of the referencing system depends in particular on the positions at which the operating staff are positioned within the operating theater and on where apparatus which might obscure the field of view of the cameras are positioned. It is known that different operations may require different apparatus and positions. Suitably positioning and aligning the cameras is thus difficult and in some situations may not be possible.

In other referencing systems, the cameras are therefore either suspended from the ceiling of the operating theater or attached at other suitable points in the operating theater. It can nonetheless easily transpire that the field of view of one or more cameras may be obscured at the same time, making referencing impossible. Positioning the cameras at a comparatively long distance from the relevant area in which three-dimensional spatial co-ordinates are to be detected also has the disadvantage that the camera will be obscured by personal, equipment and that the resolution of the image will compromise the referencing accuracy.

A system to provide navigation referenced to the patient is needed to avoid these limitations.

Inertial guidance, the tracking of an object by integrating the linear and rotational acceleration of an object over time has been used for decades to track objects including ballistic missiles, ships automobiles and other objects where the initial position and direction are known and the object is moving. These systems are very accurate and have improved remarkably over time but they all suffer from accumulated errors and motion that is outside of the sensor range. This latter problem can accumulate errors for very slow drift below the sensor sensitivity limits and for sudden large motion such as a shock caused by impact that are outside the sensor range.

During the cold war nuclear ICBM were targeted at hardened missile silos. The concept was to disable or destroy the enemy's missiles before they could be launched. To destroy a hardened silo a nuclear weapon needed to be delivered precisely with a small warhead or with less precision using a larger warhead. Use of large warheads reduces the number that could be delivered per missile launch. Thus precise delivery was of strategic benefit. During that era, inertial guidance suffered from accumulated errors in launch conditions, transiting the atmosphere, reentering the atmosphere and again transiting the atmosphere. There errors determine how accurately warheads reached their target. An improvement to this was developed called terminal guidance.

With terminal guidance, aerial images of the target area were obtained, typically from satellite. The target was precisely located relative to the landscape surrounding the target. Processing software and imaging systems in the warhead matched the stored image to that obtained in real time from the imagers. Correction to the missile trajectory was accomplished by a variety of means using the inputs from the terminal guidance system.

Over the decades, inertial guidance improved with laser ring gyros among other improvements to both hardware and software. Overall accuracy improved dramatically with terminal guidance further improving the targeting precision and accuracy.

More recently smart phones began incorporated MEMS based gyros, accelerometers, and magnetometers, often combined into one chip, to detect the direction, pointing and orientation relative to the environment, of the device. This allowed such applications as pointing the phone at the sky and displaying the astronomical features in that direction. Combined sensor based system in the 1960s could cost several hundred thousand dollars and take a cubic foot or more for the system. Today MEMS based sensors are combined into integrated circuits 3 mm×3 mm×0.9 mm with on-chip ADC and processors to combine the data into full nine-axis spatial data: six axes of position and rotation and three axes relating those positions to the earth's magnetic field. This technology continues to evolve due to the demands of wearable devices and smart phones but accumulated drift still limits the pointing accuracy of devices and tools attached to them over motion and time.

Cameras in smart phones are only a cubic centimeter in volume or less and exceed 10 megapixels in resolution. This technology is rapidly evolving and provides the tools need for neuronavigation.

SUMMARY OF THE INVENTION

The invention encompasses medical reference navigation systems for directing energy or tools at a specific point inside of the body from a specific direction, relying on CT or MRI images of the patient, and a method of aligning the image with a navigation system such that a physician can precisely deliver the therapy.

The tools and the room fiducials are coordinated or referenced to each other at the beginning of the surgical procedure using imaging. In one embodiment camera images referencing fiducial marks or features in the room are a primary means of locating the tools and the patient relative to one another, as to position and orientation. Images are fed to a computer and calculations made, as explained below. Inertial guidance can provide supplemental position/orientation data based on the motion of the tool and does not rely in any outside equipment. This can be effective if coordination with room fiducials is temporarily lost. Inertial guidance alone could provide the coordinate motion for the tool and the patient but unacceptable errors would tend to accumulate. The system of the invention can use integrated MEMS sensors or other suitable multi-axis sensors for inertial guidance and miniature cameras for optical coordination. The sensors must be sufficiently small with low mass to allow multiple sensors to be placed on the handle of surgical tools, forehead tools for locating the patient and other tools such as surgical microscopes. The multiaxis sensors are embedded in the tool handle or other device along with one or more cameras. The combination of inertial guidance and camera vision provide the robust reference navigation system of the invention. In another embodiment the cameras provide all the guidance without the need for inertial guidance.

In all reference navigation systems the various components must be referenced to each other and the patient to provide the guidance necessary to provide the precision needed. Generally the various tools and devices are referenced to each other first and then to the patient.

In one embodiment each tool can be placed in a cradle (base station) or other referencing points, with a known location to start the guidance. After each tool is located and referenced, it continuously reports its multiaxis coordinates to the base controller. In a preferred embodiment, each tool's cameras view the room (fiducials), as do cameras on the patient, and determine the coordinates and orientations of both. This allows the room to be the reference for the tools and the patient.

For reference navigation to be used it is necessary to align or fuse the patient's CT or MRI image with the patient. This is done by imaging the patient's exterior features (e.g. the face/head) with the patient in a known location in the room. A tool or headband with cameras is attached to the patient, generally on the forehead, to provide the patient coordinates when the external images are taken. This enables fusing the CT and MRI 3D image, in the computer, with the patient's head (or other region for surgery). Aligning the patient with the image data can be achieved using any type of tool that recognizes the patient location and is in communication with the computing means. Once the tool identifies several surface locations on the patient that correspond with the same location in the reconstructed CT or MRI images of that patient, the two can be fused or coordinated. After alignment is accomplished, the CT image will remain with the patient's head regardless of movement, in the display of the patient.

One convenient method to carry out the alignment is to use a smart phone, which generally has both a camera and inertial guidance as part of the device and can include additional cameras as described above, to more accurately locate the camera and its pointing angles within the room. Aiming the phone's camera at the patient's face while knowing the location and pointing direction of the phone allows matching of the CT or MRI image to the phone image being displayed. The physician can ensure that the images merge or fuse correctly or the software can carry this task out automatically. Other methods for merging or fusing the patient's location with the CT or MRI image can consist of an optical system that uses converging beams of light that scan the patient's face. When the beams appear to converge at the surface of the patient, the correct tool to patient distance is determined. An alternate method is to use a line of light scanned over the patient's face and viewed from an angle to determine the 3D profile of the subject face. Still another method to locate the patient's landings is to use a pair of miniature cameras on the alignment tool and reconstruct the patient's location from the stereo image. Another method of merging or fusing includes using a smart phone or similar device with built-in stereo cameras to provide a direct 3D image from the phone to merge or fuse with the 3D CT or MRI image.

Another aspect of the invention is to add inertial guidance to the current IR camera guidance systems used in neurosurgery (described above) and use the current IR camera data to provide the update for the inertial guidance. The advantage of this approach is to reduce the line-of-sight interruption problem by allowing the inertial guidance to bridge the gap between IR camera updates when the targets are blocked. An additional advantage of adding inertial guidance to the IR system is there are many systems in use that could benefit from this enhancement.

Another method of this invention is to use a smart phone to merge or fuse the CT or MRI data to the patient and then allow the physician to see the patient on the smart phone screen but replacing the real time image of the patient with the reconstructed CT or MRI image. In this way the physician can appear to "look" internally within the patient and see what would be visible if the smart phone were viewing in x-ray or nuclear magnetic imaging modes. This could including segmented internal structures, color coded for clarity.

The active tools described can take advantage of the very low power and low cost of hardware for power management, wireless communication and 3D processing. The array of wireless options, WiFi, Bluetooth, ZigBee, Ultra Wide Band (UWB) among others are implemented in low power, compact chip sets. To avoid wireless transmission, optical communications could be used.

In all cases described above the CT or MRI data can be considered to be individual image sets or the merging of the two together or with other imaging modalities including enhanced images with segmentation of structures including blood vessels, organs or structures within the body.

A principal object of the invention is to avoid costly existing systems for accurate guidance of surgery tools, energy beams and microscopes, particularly in brain surgery, with the provision of a simple, inexpensive and accurate guidance system. These and other objects, advantages and features of the invention will be apparent from the following description of a preferred embodiment, considered along with the accompanying drawings.

DESCRIPTION OF PREFERRED EMBODIMENTS

Figure 1:
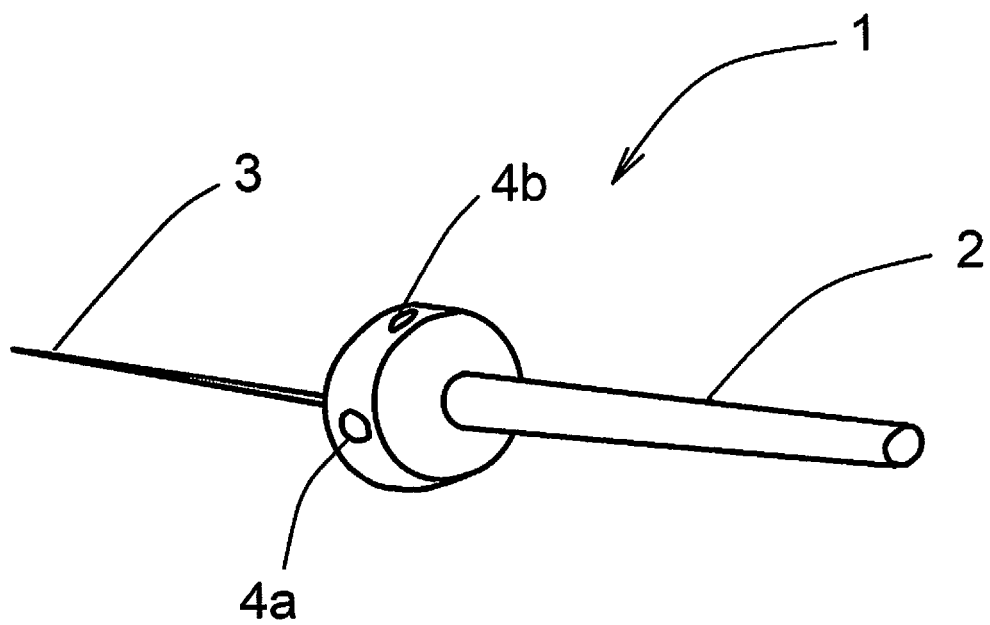
FIG. 1 is a diagram of a tool or device with cameras.
Figure 2:
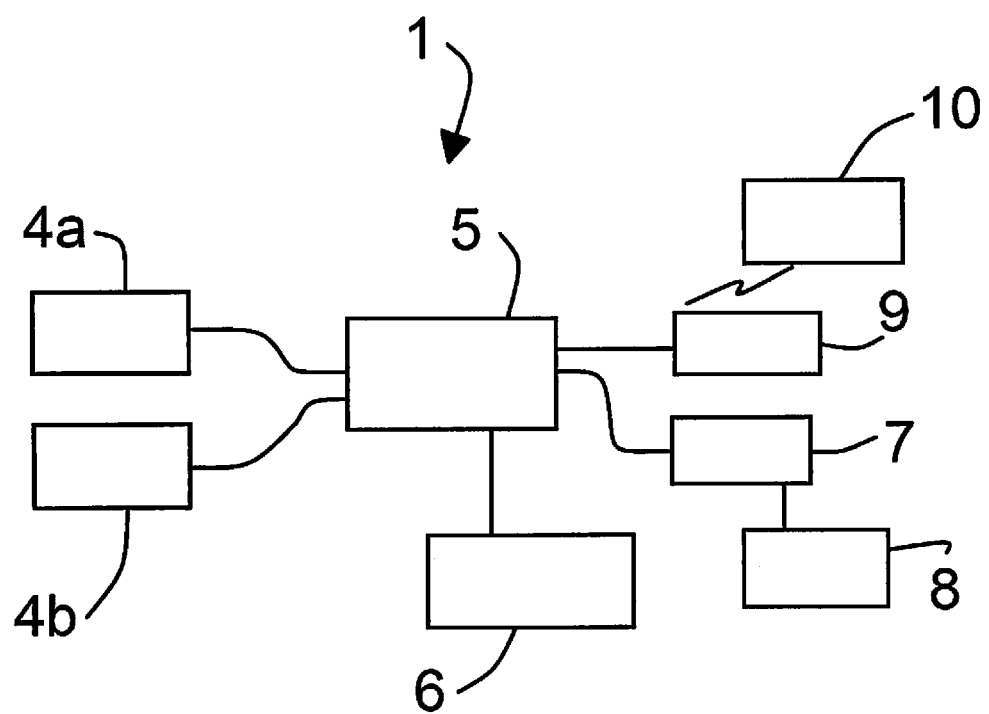
FIG. 2 is a block diagram of the active tool or device and its connection to the base controller.

FIG. 1 depicts a tool or device 1, which could be a drill, scalpel, etc., or a microscope, the tool consisting of a handle 2, one or more cameras 4a and 4b, and a tool tip 3. A block diagram of the active tool or device 1 is shown in FIG. 2. The camera or cameras 4a and 4b are connected to a computer means 5, which preferably also gets input from an inertial guidance means 6. Power for the active tool can be provided by a battery 7, and battery controller and power manager means 8. Wireless communication means 9 provides tool or device location and orientation to a base controller 10.

Figure 2A:
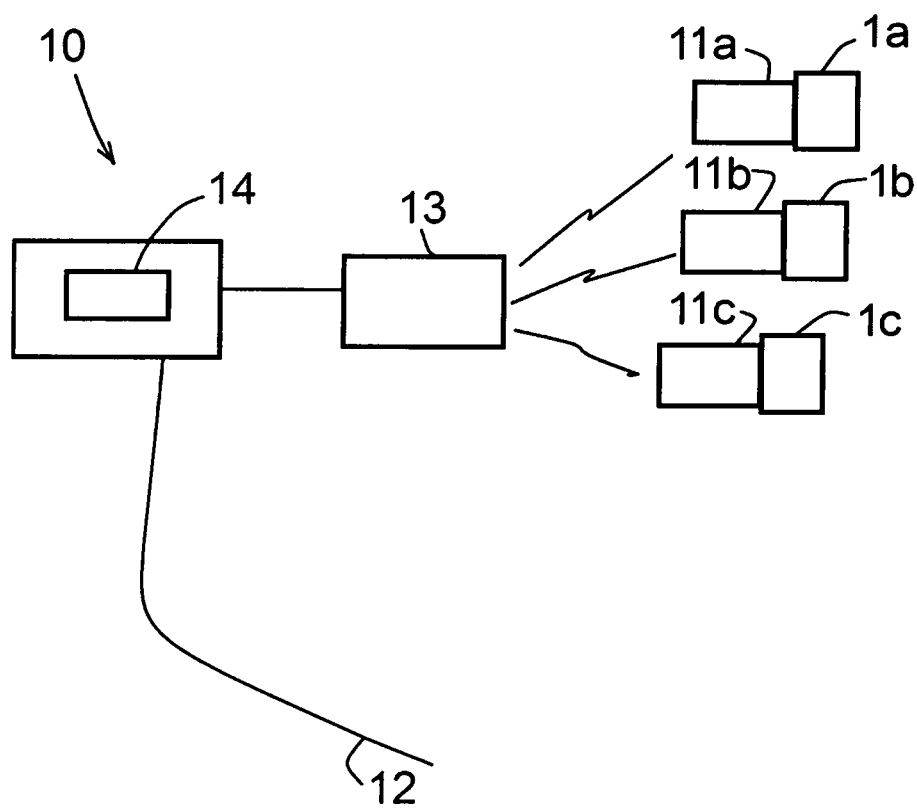
FIG. 2A is a block diagram of the base controller.

A block diagram of the base controller is depicted in FIG. 2A. The base controller 10 uses computer means 14 to process inputs from camera means 11a-11c (powered by line power 12), via wireless communications means 13 to receive location and orientation data from the tools 1a-1c.

Figure 2B:
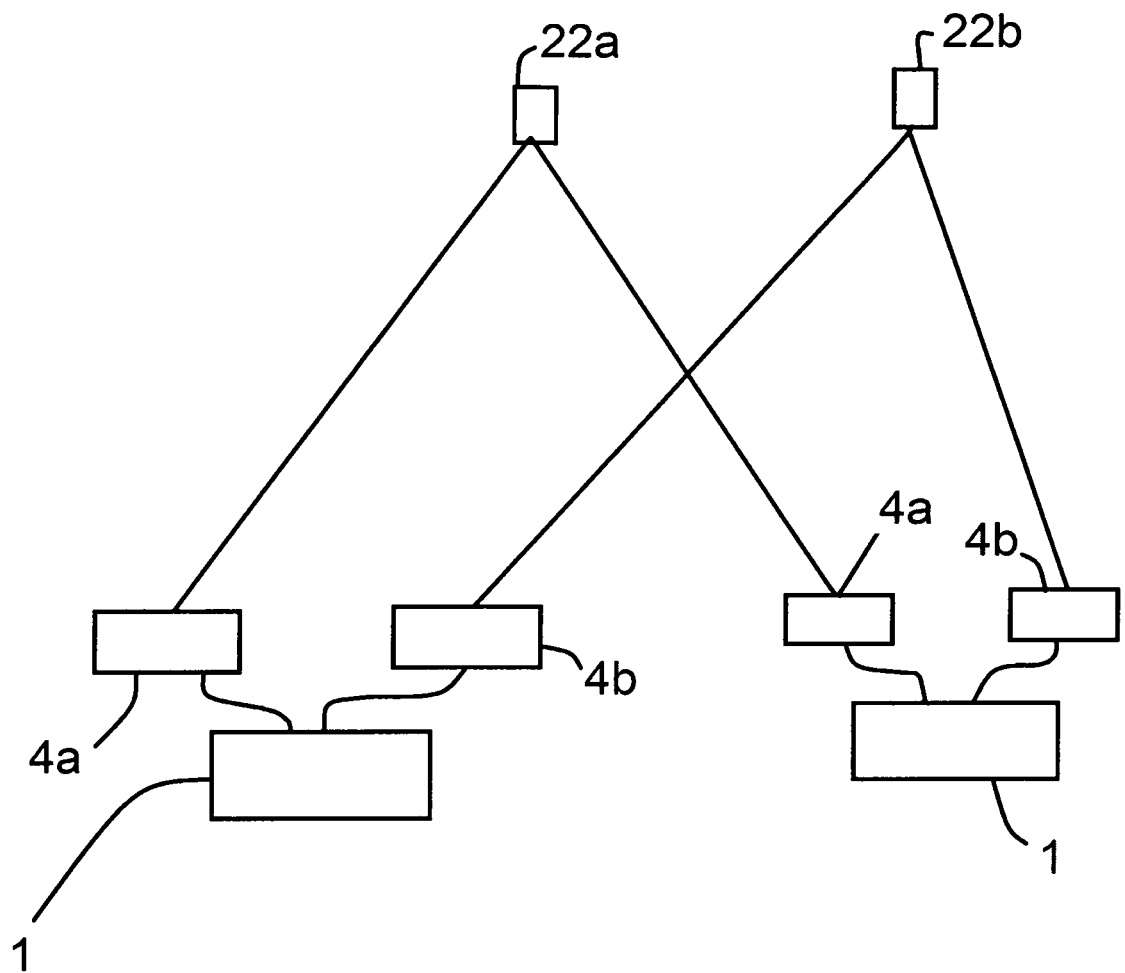
FIG. 2B is a diagram of the base controller and a tool viewing the same fiducials.

FIG. 2B depicts the tool 1 with two cameras 4a and 4b, in two different positions within a room having fiducials 22a and 22b. When the tool 1 is in a first position the angles that the cameras make with fiducials 22a and 22b are as seen, but when the tool 1 is translated away to the second position, the angles the camera makes with the fiducials change as shown providing the data needed to calculate the amount of translation, or simply the new position in the room. Each different position and orientation of the tool will present a different image, with fiducials at different locations in the image, sufficient data (even with a single camera) to calculate precise location and orientation of the tool. Not all the rays to all the fiducials are shown in FIG. 2B for simplicity.

Figure 3:
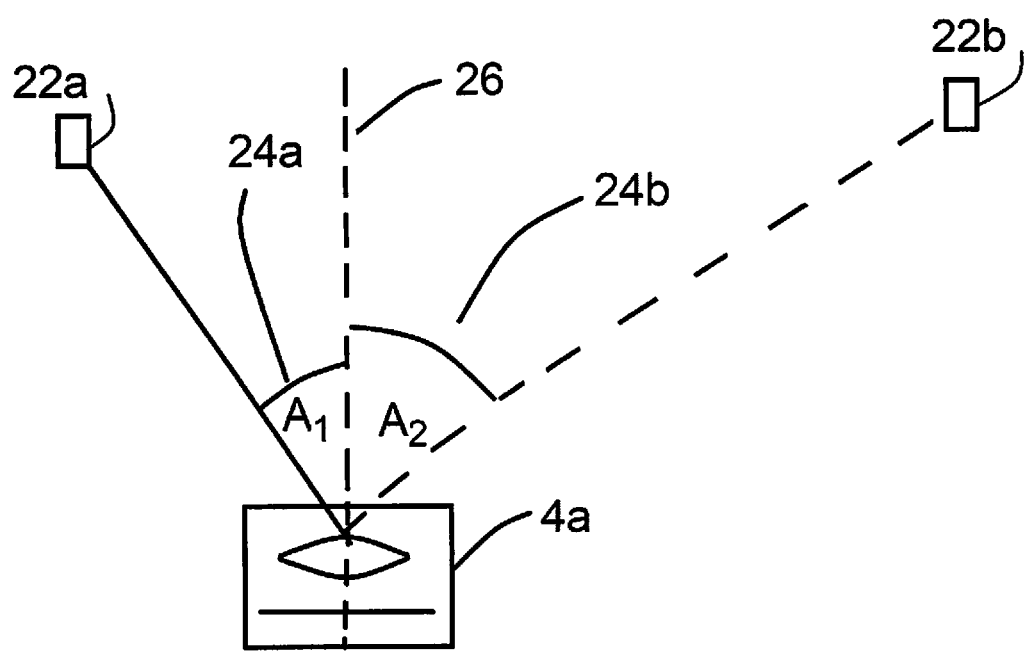
FIG. 3 is a diagram of one of the cameras viewing fiducials in the camera's field of view.
Figure 4:
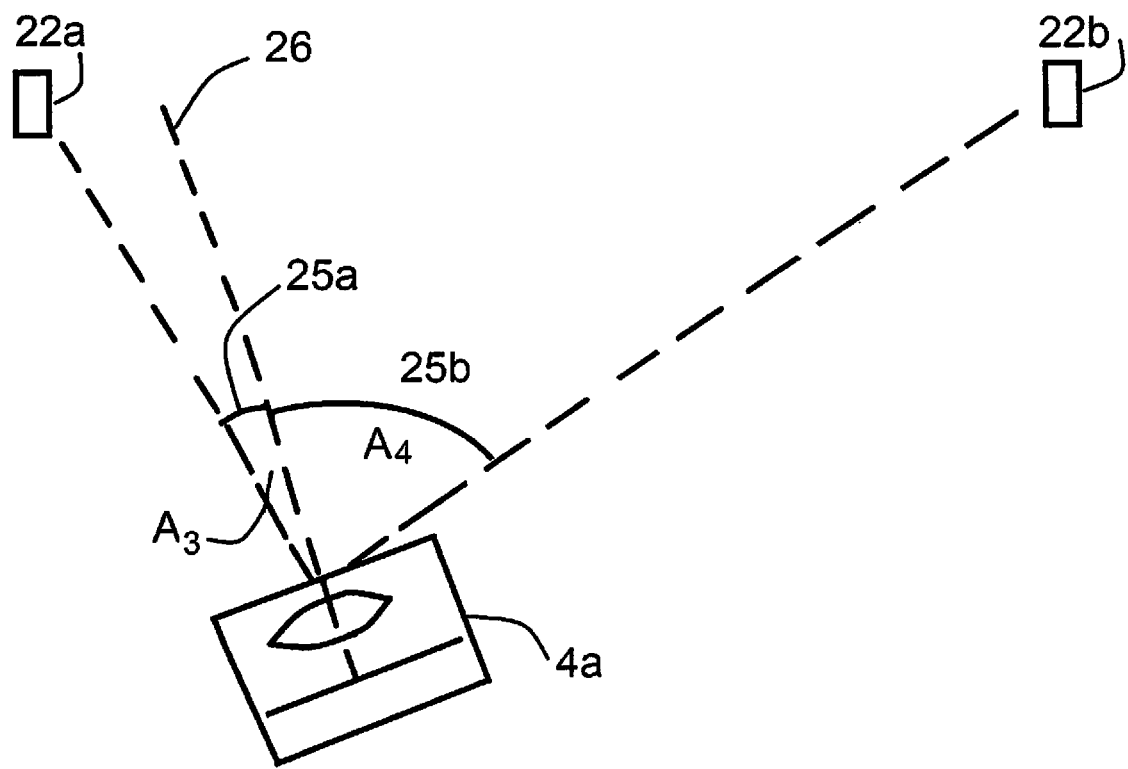
FIG. 4 is a diagram of one of the cameras viewing fiducials in the camera's field-of-view after rotation of the tool or device.

FIG. 3 depicts one of the tool cameras 4a, viewing fiducials 22a and 22b, making angles $A_1$ and $A_2$ to the camera axis. When the tool with camera 4a is rotated as shown in FIG. 4 the fiducials 22a and 22b make new angles $A_3$ and $A_4$ to the camera axis 26, and the fiducials are located at different positions in the image frame.

Figure 5:
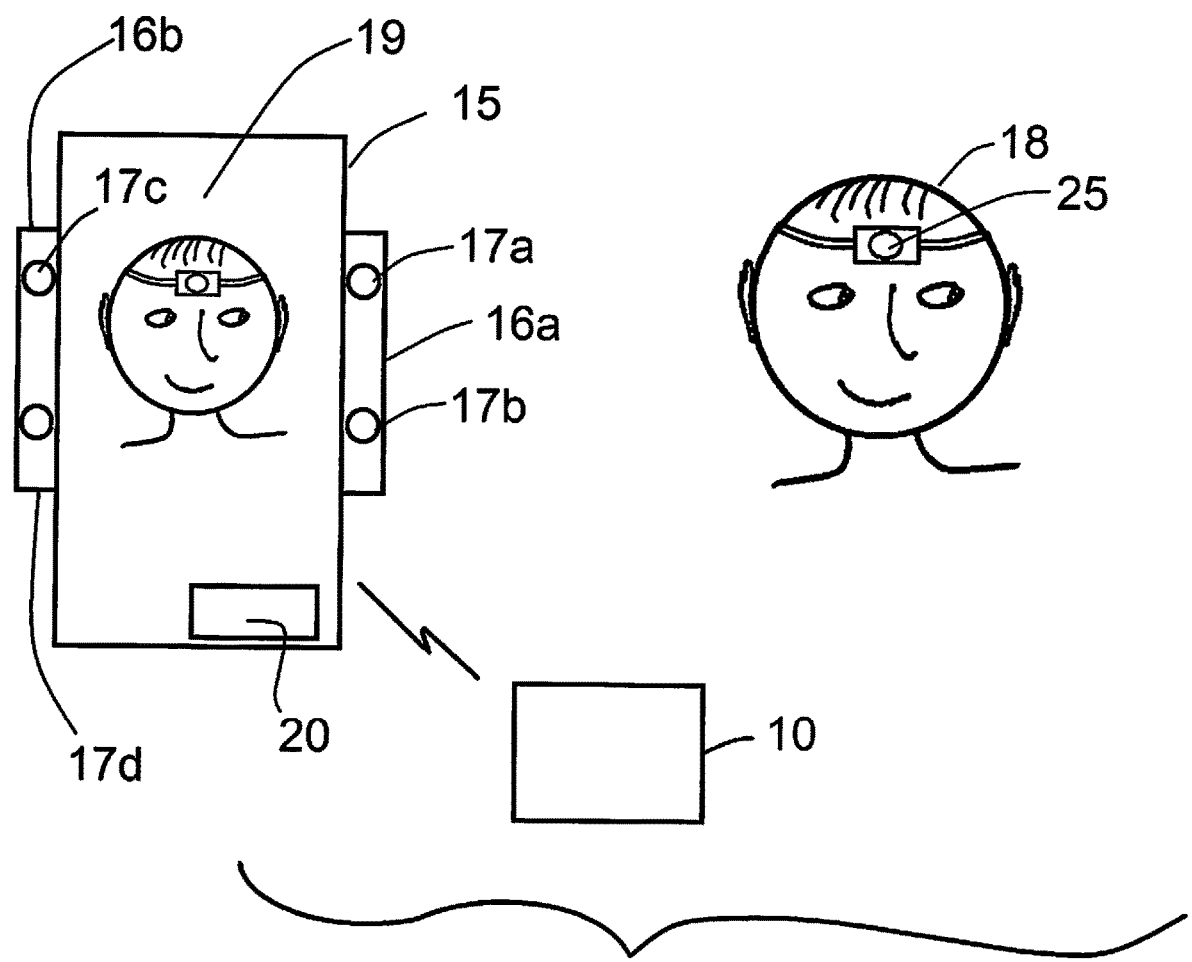
FIG. 5 shows a subject being viewed by a smart phone to determine location of the subject.

FIG. 5 shows a subject 18, viewed by a smart phone, tablet or other camera device with an integrated display 15, displaying an image 19 of the subject. The smart phone, tablet or other camera device (or a holder for the device) can have handles 16a and 16b, containing one or more cameras 17a-17d. The phone, tablet or other display device displays the real-time image 19, determining exactly where the patient's head is located and oriented in the room. This image is then merged or fused in the computer with a scan or a virtual image from a CT or MRI of the patient's head. This ties the CT scan image to the patient. After this one-time imaging of the patient's external features, and the merging with the CT or MRI scan image, the CT will follow the patient's head movements (and rotations) with no further external imaging needed. The patient has one or more cameras 25 attached to the head, so that fiducials in the room are always monitored, allowing the position and orientation of the head to be calculated and displayed in real time, with the three-dimensional CT scan imposed with the head image. Relative positions and orientations of the patient and of surgical tools (drill, scalpel, microscope, etc.) are continuously known and displayed.

The external image of the patient can be taken using a fixed camera, e.g. one connected to the console or otherwise anchored in a known position in the room, to image the patient in precise location and orientation.

Figure 6:
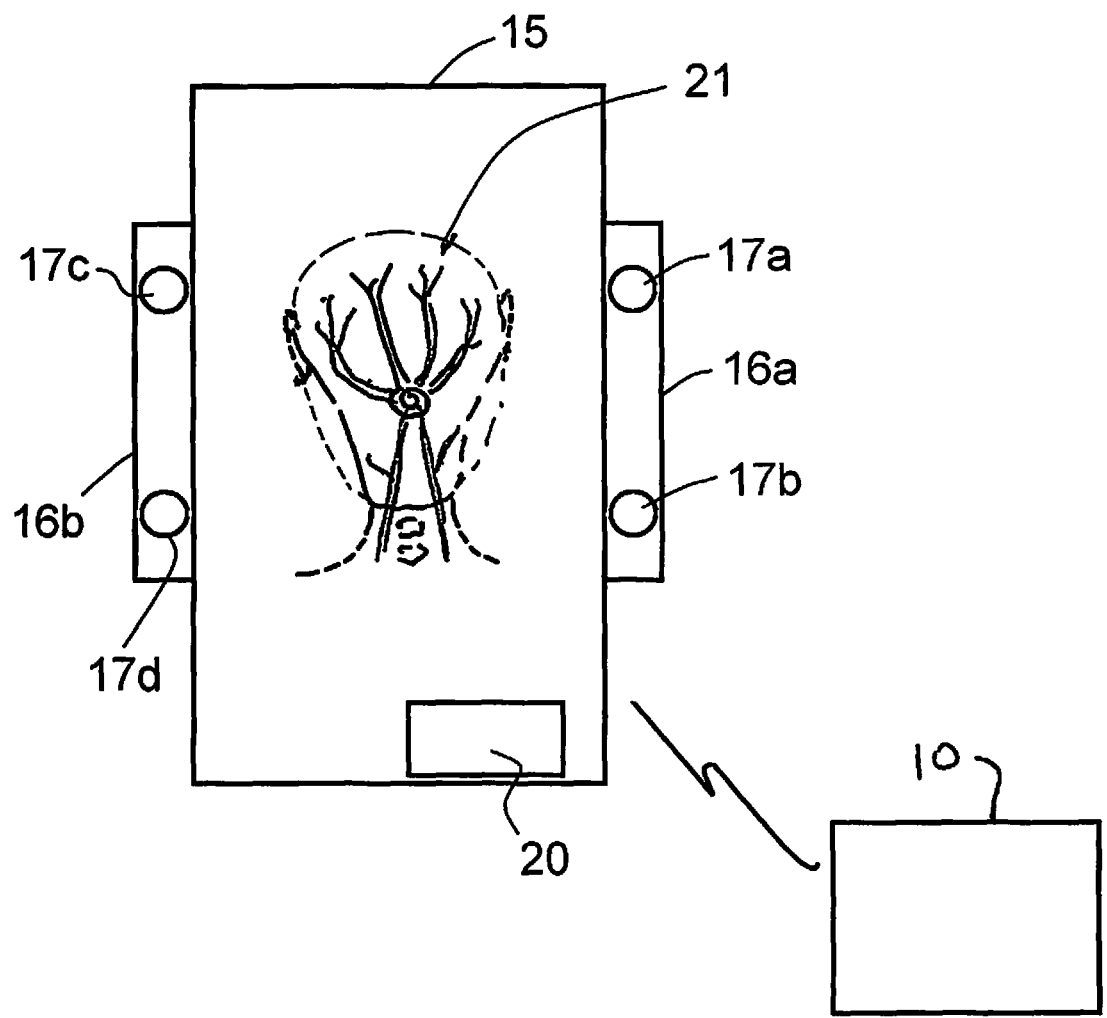
FIG. 6 shows a subject being viewed by a smart phone and displaying a CT or MRI derived image where the subject's image would be.

FIG. 6 shows the same smart phone, tablet or other device 15 displaying an image 21 derived from the patient's CT or MRI image, overlaid or merged with the live (external) image 19 of the patient. The image 21 shown displays the neurovasculature or brain tissue of the patient, along with the outline and external features of the patient's head, as if the head were transparent or partially transparent, this image being presented in real time. This illustrates that the procedure could be monitored and guided for the surgeon using a smart phone or larger tablet computer, rather than a monitor on a fixed console.

Whether a fixed camera is used to image external features of the patient and to register the exact position of the patient at the time of the imaging, or a smart phone or tablet 15 is used as in FIG. 5, this registration of the external features with the exact position of the patient in the room needs no further updating using the smart phone or fixed camera. The cameras 25 mounted on the patient (which could be on a headband, for example), are monitoring the fiducials in the room and thus the computer can always determine the exact position and orientation of the patient's head during the entire procedure. The CT scan is thus tied to the image of the patient regardless of movement. The computer could present the image in a way that the image of the head does not move on the screen, even though the patient actually moves, by simply showing relative positions of the surgical tools to the head. Alternatively, the display can show the head as it moves and in changing positions.

The invention is described above with reference to brain surgery, but it is applicable to other surgeries as well, such as hip or knee surgeries and other surgeries.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. A method for monitoring location and orientation of a surgical tool relative to a surgical site on a patient in preparation for and during a surgical procedure conducted in a room on the surgical site, comprising steps of:

securing to the patient at least one site camera near the surgical site with wireless means to communicate with a computer means, and sending site camera image data from the at least one site camera to the computer means, providing said surgical tool with at least one tool camera with wireless means to communicate with the computer means, and sending tool camera image data from the at least one tool camera to the computer means, providing to the computer means an internal scan image of the patient at the surgical site, providing to the computer means an image of the patient's external features with the patient in position for the surgical procedure, overlaying, with the computer means, the internal scan image with the patient's external features at and adjacent to the surgical site, to produce overlaid image so that the internal scan image is registered to the patient's external features regardless of patient movement, repeatedly calculating in real time relative positions and orientations of the surgical tool and the surgical site of the patient using as fiducials, tool camera image data of fixed features of the room and site camera image data of the fixed features of the room, said calculating being based on the fiducials making different angles with the at least one tool camera and with the at least one site camera with movements of the surgical tool or the surgical site, and presenting the overlaid image on a monitor in real time imposed with indications of positions and orientations of the surgical tool relative to the surgical site as the surgical procedure is performed, without displaying images from said site and tool cameras.

2. The method of claim 1, further including using inertial guidance to produce additional backup data relating to the relative positions and orientations of the surgical tool and the surgical site.

* * * * *